United States Patent [19]

Choudhary et al.

[11] Patent Number: 5,118,654
[45] Date of Patent: Jun. 2, 1992

[54] PROCESS FOR THE PREPARATION OF AN IMPROVED LI-PROMOTED MGO CATALYST USEFUL FOR OXIDATIVE COUPLING OF METHANE TO ETHANE AND ETHYLENE

[75] Inventors: Vasant R. Choudhary; Meenakshi Y. Pandit; Sopan T. Chaudhari, all of Maharashtra, India

[73] Assignee: Council of Scientific & Industrial Research, New Delhi, India

[21] Appl. No.: 748,772

[22] Filed: Aug. 22, 1991

[51] Int. Cl.5 .................. B01J 37/04; B01J 21/10; B01J 23/04
[52] U.S. Cl. ................... 502/340; 585/500; 585/943
[58] Field of Search ............. 502/340; 585/500, 943

[56] References Cited

U.S. PATENT DOCUMENTS 4,517,398  5/1985  Sofranko .................. 585/500
4,997,802  3/1991  Matsuura et al. ........ 502/340 X
5,077,446  12/1991  Kolts et al. ............... 585/500

FOREIGN PATENT DOCUMENTS 62-129227  6/1987  Japan .................. 585/500
86/07351  12/1986  World Int. Prop. O. ...... 585/500

Primary Examiner—W. J. Shine
Assistant Examiner—Douglas J. McGinty
Attorney, Agent, or Firm—Ladas & Parry

[57] ABSTRACT

A process for preparation of an improved Li-promoted MgO catalyst useful for oxidative coupling of methane to ethane and ethylene, in presence of free oxygen, which comprises (i) mixing thoroughly powdered magnesium acetate and lithium acetate, which are catalyst precursors, with Li/Mg mole ratio of 0.01–1.0 with or without water, the $H_2O$/magnesium acetate weight ratio being in the range of 0–5.0, (ii) heating the mixture, while stirring, to dryness at a temperature of about 60°–300°C., (iii) powdering and calcining the dried mixture at a temperature of about 500°–1000°C. in presence of air, $O_2$, $CO_2$, inert gas (like $N_2$, He, Ar, etc.) or their mixture or under vacuum for about 1–100 h and (iv) making by known methods the pellets, extrudates or granules of the catalyst of required size.

7 Claims, No Drawings

PROCESS FOR THE PREPARATION OF AN IMPROVED LI-PROMOTED MGO CATALYST USEFUL FOR OXIDATIVE COUPLING OF METHANE TO ETHANE AND ETHYLENE

This invention relates to an improved Li—MgO catalyst for oxidative coupling of methane to ethane and ethylene. This invention particularly relates to a novel process for preparation of an improved lithium oxide containing MgO catalyst for direct conversion of methane by its partial oxidation to ethane, ethylene and higher hydrocarbons. The process of the present invention could be used by catalyst manufacturers and producers of ethylene, and also by producers of ethane and higher hydrocarbons as well as by ethylene users, for examples, those make petrochemicals, plastics, fibres, elastomers, plasticizers, etc.

Methane is a major constituent of natural gas and also of biogas. It is being seriously considered as an alternative source of hydrocarbons and petrochemicals in the future. The conventional processes, which involve $C_1$-Chemistry for the production of methanol, aliphatic hydrocarbons and oxygenated hydrocarbons from methane require the intermediate formation of synthesis gas. These processes suffer from the requirement of complicated engineering steps and also from the relative inefficiency of carrying out extensive oxidation of methane to carbon monoxide and then reduction of carbon monoxide to methanol or aliphatics and oxygen containing compounds. Therefore, a single step conversion process of methane to ethylene (which can be further converted to easily transportable products such as liquid hydrocarbons and to ethylene-based petrochemicals) can have far reaching economic implication. Methane is most inert among the hydrocarbons and hence its direct conversion to ethylene is very difficult. Therefore, direct conversion of methane to ethylene is a great challenge.

In the prior art, Li-promoted MgO (or Li—MgO) is known for its catalytic activity in oxidative coupling of methane to $C_2$-hydrocarbons (viz. ethane and ethylene). Lunsford and Co-workers [Nature, Vol. 314, p. 721-722, (1985); J. Am. Chem. Soc., Vol. 107, P. 5062-5068 (1985)] have reported that Li—MgO prepared by adding high purity MgO and $Li_2CO_3$ to deionised water and evaporating the water, while stirring, until only a thick paste is formed and then drying the paste at 140° C. for 5 h and calcining it at 465° C., could be used as catalyst for converting methane by its partial oxidation with free oxygen to ethane and ethylene in high yields at 720° C.

Henry and Lunsford [Eur. Patent Appl. EP 196,541, Oct. 08, 1986; U.S. application Ser. No. 713,653, Mar. 19, 1985, now U.S. Pat. No. 5,077,446] described a process for oxidative coupling of methane with high conversion and high selectivity to ethane and ethylene. The process comprises contacting a $CH_4$ containing gas (especially natural gas) and an oxygen containing gas (e.g. air) at 1-30:1 (volume ratio) $CH_4$—$O_2$ at 500°-1500° C. with a material containing 0.1-50 wt % Li and MgO. When 4.4:1 (volume ratio) $CH_4$—$O_2$ mixture was contacted over 7 wt. % Li—MgO at 706° C. for 5 minutes, the $CH_4$ conversion, $C_2$-selectivity and $C_2$-yield were 23.7%, 61.6% and 14.6%, respectively.

In a Japanese patent [S. Yokohama, Jpn. Kokai, Tokkyo Koho, JP. 62,129,227 Jan. 11, 1987], Li—MgO catalyst was prepared by evaporating aqueous suspension containing MgO and $Li_2CO_3$ to dryness, heating at 550° C. for 1 h and annealing at 1000° C. for 10 h.

Although Li—MgO catalyst prepared by the process described above shows good activity (i.e. methane conversion) and selectivity for $C_2$-hydrocarbons in oxidative coupling of methane, its deactivation during the catalytic process is very fast [Ref. J. R. H. Ross and co-workers, J. Chem. Soc. Chem. Commun., P. 1433-1434 (1987); J. H. Lunsfords and co-workers, J. Am. Chem. Soc., Vol. 107, P. 5062-5068, 1985; V. R. Choudhary and co-workers, "Recent Trends in Chemical Reaction Engineering", vol. 1, Eds. B. D. Kulkarni, R. A. Mashelkar and M. M. Sharma, Wiley Eastern Ltd., Delhi, p. 90-105, 1987]. The catalyst shows a very sharp decrease in its catalytic activity (i.e. methane conversion and yield for $C_2$-hydrocarbons) during the initial period of 10 hours in the catalytic process. Another disadvantage of the above process for preparation of Li-promoted MgO catalyst is that the reproducibility of catalyst is poor because of a use of MgO in the catalyst preparation. This is because of the fact that MgO is not a well defined or specified material. MgO has a highly defected structure and therefore, exists in different forms having different surface properties, depending upon its process of preparation and impurities in it.

Recently, Matsuura and Yoshida [Eur. Patent Appl. EP 320,301 Jun. 14, 1989, JP. Appl. 87/312, 127 Dec. 11, 1987, U.S. Pat. No. 4,997,802] have described a catalyst comprising a single crystal high purity and ultra fine-powdered MgO obtained by the gas method and a lithium oxide for preparation of $C_2$-hydrocarbons by oxidative coupling of methane. The Li—MgO catalyst was prepared by heating magnesium at 1200° C., contacting the Mg-vapours with air, adding the resulting single-crystal ultra fine MgO to an ethanol solution of lithium acetylacetonate, drying and calcining at 800° C. The catalyst in a fixed bed was used to oxidize 2:1 $CH_4/O_2$ gas at 800° C. producing ethane and ethylene with $C_2$-selectivity of 52.5%.

Although, the Li—MgO catalyst prepared by the use of ultra fine crystalline MgO is very active for the oxidative coupling of methane to $C_2$-hydrocarbons [Ref. Matsuura et al. Appl. Catal. Vol. 47, P. 299-306, 1989], it is very expensive because of the high cost of production of ultra fine crystalline magnesium oxide from magnesium. Also, the catalyst shows poor selectivity for $C_2$-hydrocarbons.

The main object of the present invention is to provide a novel process for preparation of Li-promoted MgO catalyst for oxidative coupling of methane to ethane and ethylene, using magnesium acetate and lithium acetate as the catalyst precursors. So far, no catalyst preparation process involving use of magnesium acetate and lithium acetate as precursors for catalyst components viz. magnesium oxide and lithium, respectively, for the preparation of Li-promoted MgO catalyst has been described in the prior art.

The main finding of the present invention is that Li-promoted MgO catalyst, showing high methane conversion activity, high selectivity and yield for $C_2$-hydrocarbons and also high stability or long life in oxidative coupling of methane to ethane and ethylene, can be prepared using magnesium acetate and lithium acetate as precursors for MgO and Li, respectively.

Accordingly, the present invention porovides a process for the preparation of an improved Li-promoted MgO catalyst useful for oxidative coupling of methane to ethane and ethylene, which comprises (i) mixing thoroughly magnesium acetate and lithium acetate which are catalyst precursors, with Li/Mg mole ratio of 0.01-1.0 with or without water, the H₂O/magnesium acetate weight ratio being in the range of 0-5.0, (ii) heating the mixture, while stirring, to dryness at a temperature of about 80°-300° C., (iii) powdering and calcining the dried mixture at a temperature of about 500°-1000° C. in presence of air, $CO_2$, inert gas (like $N_2$, He, Ar, etc.) or their mixture or under vacuum for about 1-100 h and (iv) making by known methods pellets, extrudates or granules of the catalyst of required size.

The preferred Li/Mg mole ratio in the mixture of catalyst precursors may be in the range of 0.02-0.5, the preferred H₂O/magnesium acetate weight ratio may be in the range of 0.0-1.0, the preferred temperature range for heating the mixture of catalyst precursors may be in the range of 100°-150° C., the preferred calcination temperature may be in the range of 700°-800° C., the preferred period of calcination may be in the range of 2-20 h, and the preferred gas atmosphere for the calcination may be static air or air containing about 2-20 mol % $CO_2$.

According to a feature of the invention, the mixture of catalyst precursors (i.e. magnesium acetate and lithium acetate) may be prepared by reacting magnesium oxide or hydroxide or carbonate and lithium carbonate or hydroxide with concentrated acetic acid in stoichiometric amounts at 95°-100° C. until the completion of the reaction.

The product obtained from the process of the invention is an improved Li-promoted MgO catalyst useful in catalytic oxidative coupling of methane to ethane and ethylene.

The present invention reveals that an improved Li-promoted MgO catalyst showing high methane conversion activity, high $C_2$-selectivity and yield and long catalyst life in the oxidative coupling of methane to $C_2$-hydrocarbons can be prepared using magnesium acetate and lithium acetate as catalyst precursors, by the catalyst preparation process described in the invention.

Using the improved Li-promoted MgO catalyst prepared by the process of the present invention in oxidative coupling of methane in presence of free oxygen, methane can be converted to higher hydrocarbons (mainly ethylene, ethane and $C_{3-4}$ hydrocarbons) at very high conversion and selectivity with high space-time-yield (STY) or productivity for $C_{2+}$ hydrocarbons, without loss of catalytic activity (or without catalyst deactivation) for long period. For example, 53-81% $C_{2+}$ selectivity, 14-37 mmol.g$^{-1}$.h$^{-1}$ $C_{2+}$ productivity (or $C_2$-space-time-yield) at methane conversion of 18-40% could be achieved in the oxidative coupling of methane over an improved Li-promoted MgO catalyst prepared by the process of present invention, without loss of catalytic activity (or without catalyst deactivation) at least for an initial period of 15 hours in the catalytic process.

The practice of the present invention is further described with reference to the following examples. These are provided for illustrative purpose only and are not to be construed as limitations on the invention.

DEFINITIONS OF TERMS USED IN THE EXAMPLES $$\text{Total conversion of methane (\%)} = \text{mol \% of methane converted to products.}$$

$$\text{Selectivity for a particular product (\%)} = \frac{\text{Conversion of methane to the product (\%)}}{\text{Total conversion of methane (\%)}} \times 100$$

Productivity or Space-Time-Yield (STY) of a particular product is the amount of the product formed in the process per unit weight of catalyst per unit time.

Space Velocity is the volume of gaseous reactant (at STP) passed over a unit weight of catalyst per hour.

Conversion of methane given in the examples is per pass conversion. $C_{2+}$ hydrocarbons means hydrocarbons containing 2 and more than two carbon atoms in their molecules.

The invention is illustrated with the following examples which should not be construed to limit the scope of the invention.

EXAMPLE 1

53.61 gms of magnesium acetate [$(CH_3COO)_2Mg.4H_2O$], 2.55 gms of lithium acetate [$(CH_3COO)Li.2H_2O$] and 30 gms of deionised water were thoroughly mixed and then heated at 100° C. with constant stirring until a dried mass was obtained. The dried mass was powdered and then calcined in a muffle furnace under static air at 750° C. for 6 hrs. The calcined material was pressed binder-free and crushed to 22-30 mesh size particles to provide the desired Li-promoted MgO catalyst. The Li/Mg mole ratio before and after the calcination of the catalyst was 0.1 and 0.09, respectively. The colour of the catalyst was gray.

EXAMPLE 2

This example illustrates the properties and stability or life of the catalyst, the preparation of which is described in EXAMPLE-1, in oxidative coupling of methane to $C_2$-hydrocarbons.

Catalyst Properties

The surface area of the catalyst was determined by single point BET method by measuring the adsorption of nitrogen at liquid nitrogen temperature and at nitrogen concentration of 30 mol % (balance helium) using Monosorb Surface Area Analyser (Quanta Chrome Corp., U.S.A.) based on dynamic adsorption/desorption technique.

The surface area of the catalyst was 7.0 m².g$^{-1}$. The $CO_2$ content of the catalyst was measured as follows. The catalyst (0.5 gm) was packed in a flow quartz reactor and pretreated insitu at 750° C. in a flow of pure $N_2$ (20 cm³.min$^{-1}$). The catalyst temperature was then increased from 750° C. to 1000° C. and maintained at 1000° C. for 30 min. The $CO_2$ evolved from the catalyst in the above temperature step was measured quantitatively by absorbing it completely in a saturated solution of barium hydroxide and measuring the $BaCO_3$ formed gravimetrically.

The $CO_2$ content of the catalyst was 0.33 mmol.g$^{-1}$.

Performance of Catalyst in Oxidative Coupling of Methane to $C_2$-Hydrocarbons The oxidative coupling of methane to $C_2$-hydrocarbons reaction over the catalyst was carried out at atmospheric pressure in a flow quartz reactor (i.d.: 10 mm) packed with 0.5 gm catalyst using a mixture of pure methane and $O_2$ as a feed. The reactor temperature was measured by Chromel-Alumel thermocouple located in the catalyst bed. The reactor effluent gases were cooled by water condenser and then analysed for ethane, ethylene, higher hydrocarbons, carbon dioxide, carbon monoxide and unconverted methane and oxygen by an on-line gas chromatograph using a Porapak-Q and Sphercarb columns. Before carrying out the reaction, the catalyst was pretreated insitu at 750° C. in a flow of pure $N_2$ (30 $cm^3.min^{-1}$) for one hour.

The catalyst performance was evaluated at the following process conditions.

Feed composition: 80 mol % $CH_4$ and 20 mol % $O_2$
Space velocity: 10,300 $cm^3.g^{-1}.h^{-1}$
Reaction temperature: 745° C.
Time-on-stream: 15 hr.

The results showing catalyst stability of life in the oxidative methane coupling process are given below.

| Time-on-Stream (hr): | 0.25 | 1.0 | 3.0 | 5.0 | 7.0 | 10.0 | 12.0 | 15.0 |
|---|---|---|---|---|---|---|---|---|
| $CH_4$ Conversion (%): | 28.5 | 28.8 | 28.7 | 28.5 | 28.6 | 28.7 | 28.3 | 28.1 |
| $C_2$-selectivity (%): | 57.5 | 57.6 | 58.7 | 57.3 | 57.7 | 57.1 | 57.6 | 57.4 |
| $C_{2+}$ Selectivity (%): | 65.8 | 65.6 | 66.1 | 65.6 | 65.4 | 64.9 | 65.0 | 65.3 |

EXAMPLE 3

This example illustrates the performance of the catalyst, the preparation of which is described in EXAMPLE-1, in oxidative coupling of methane to $C_2$-hydrocarbons at different process conditions. The oxidative coupling of methane over the catalyst was carried out at atmospheric pressure in the reactor and by the procedure similar to that described in EXAMPLE-2.

The results obtained are given in Table-1.

EXAMPLE 4

53.61 gms of magnesium acetate [$(CH_3COO)_2Mg.4H_2O$], 12.75 gms of lithium acetate [$(CH_3COO)Li.2H_2O$] and 100 gms of deionised water were thoroughly mixed and then heated at 105° C. with constant stirring until a dried mass was obtained. The dried mass was powdered and then calcined in a muffle furnace under static air at 750° C. for 6 hrs. The calcined material was pressed binder-free and crushed to 22–30 mesh size particles to provide the desired Li-promoted MgO catalyst.

The Li/Mg mole ratio before and after the calcination of the catalyst was 0.5 and 0.38, respectively. The colour of the catalyst was gray. The surface area and $CO_2$ content of the catalyst, measured by the procedures similar to that described in EXAMPLE-2, were 2.9 $m^2.g^{-1}$ and 1.03 $mmol.g^{-1}$, respectively.

EXAMPLE 5

This example illustrates the performance of the catalyst, the preparation of which is described in EXAMPLE-4, in oxidative coupling of methane to $C_2$-hydrocarbons at different process conditions. The oxidative coupling of methane over the catalyst was carried out at atmospheric pressure in the reactor and by the procedure similar to that described in EXAMPLE-2.

The results obtained are given in Table-2.

EXAMPLE 6

107.3 gms of magnesium acetate [$(CH_3COO)_2Mg.4H_2O$], 12.75 gms of lithium acetate [$(CH_3COO)Li.2H_2O$] and 80 gms of deionised water were thoroughly mixed and then heated at 120° C. with constant stirring until a dried mass was obtained. The dried mass was powdered and then calcined in a muffle furnace under static air at 750° C. for 6 hrs. The calcined material was pressed binder-free and crushed to 22–30 mesh size particles to provide the desired Li-promoted MgO catalyst.

The Li/Mg mole ratio before and after the calcination of the catalyst was 0.25 and 0.19, respectively. The colour of the catalyst was gray. The surface area and $CO_2$ content of the catalyst, measured by the procedures similar to that described in EXAMPLE-2, were 5.6 $m^2.g^{-1}$ and 0.47 $mmol.g^{-1}$, respectively.

EXAMPLE 7

This example illustrates the performance of the catalyst, the preparation of which is described in EXAMPLE-6, in oxidative coupling of methane to $C_2$-hydrocarbons at different process conditions. The oxidative coupling of methane over the catalyst was carried out at atmospheric pressure in the reactor and by the procedure similar to that described in EXAMPLE-2.

The results obtained are given in Table-3.

EXAMPLE 8

53.62 gms of magnesium acetate [$(CH_3COO)_2Mg.4H_2O$], 1.28 gms of lithium acetate [$(CH_3COO)Li.2H_2O$] and 50 gms of deionised water were thoroughly mixed and then heated at 100° C. with constant stirring until a dried mass was obtained. The dried mass was powdered and then calcined in a muffle furnace at 700° C. in air (100 $cm^3.min^{-1}$) flowing over the catalyst for 10 hrs. The calcined material was pressed binder-free and crushed to 22–30 mesh size particles to provide the desired Li-promoted MgO catalyst.

The Li/Mg mole ratio before and after the calcination of the catalyst was 0.05 and 0.04, respectively. The colour of the catalyst was gray. The surface area and $CO_2$ content of the catalyst, measured by the procedures similar to that described in EXAMPLE-2, were 11.5 $m^2.g^{-1}$ and 0.15 $mmol.g^{-1}$, respectively.

EXAMPLE 9

This example illustrates the performance of the catalyst, the preparation of which is described in EXAMPLE-8, in oxidative coupling of methane to $C_2$-hydrocarbons at different process conditions. The oxidative coupling of methane over the catalyst was carried out at atmospheric pressure in the reactor and by the procedure similar to that described in EXAMPLE 2.

The results obtained are given in Table-4.

EXAMPLE 10

107.3 gms of magnesium acetate [$(CH_3COO)_2Mg.4H_2O$] and 1.02 gms of lithium acetate [$(CH_3COO)Li.2H_2O$] were thoroughly mixed and then heated at 150° C. with constant stirring until a dried mass was obtained. The dried mass was powdered and then calcined in a muffle furnace at 800° C. in presence of $CO_2$ (20 mol %) in air flowing over the catalyst for 2 hrs. The calcined material was pressed binder-free and crushed to 22–30 mesh size particles to provide the desired Li-promoted MgO catalyst.

The Li/Mg mole ratio before and after the calcination of the catalyst was 0.02 and 0.018, respectively. The colour of the catalyst was gray. The surface area and $CO_2$ content of the catalyst, measured by the procedures similar to that described in EXAMPLE-2, were 14.1 $m^2.g^{-1}$ and 0.02 $mmol.g^{-1}$, respectively.

EXAMPLE 11

This example illustrates the performance of the catalyst, the preparation of which is described in EXAMPLE-10, in oxidative coupling of methane to $C_2$-hydrocarbons at different process conditions. The oxidative coupling of methane over the catalyst was carried out at atmospheric pressure in the reactor and by the procedure similar to that described in EXAMPLE-2.

The results obtained are given in Table-5.

EXAMPLE 12

An aqueous mixture of magnesium acetate and lithium acetate was prepared by reacting 100 gms of powdered pure MgO and 9.24 gms of lithium carbonate with 640 gms of concentrated acetic acid (50 wt/wt % in water) at 95° C. on water bath while stirring for 2 hr. The mixture was then heated at 120° C. with constant stirring until a dried mass was obtained. The dried mass was powdered and calcined in a muffle furnace under static air at 700° C. for 20 hrs. The calcined material was pelletized without using any binder to provide the desired Li-promoted MgO catalyst. The catalyst was grayish in colour. The Li/Mg mole ratio before and after the calcination of the catalyst was 0.1 and 0.09, respectively. The surface area and $CO_2$ content of the catalyst were 6.5 $m^2.g^{-1}$ and 0.31 $mmol.g^{-1}$, respectively.

TABLE 1

Results on oxidative coupling of methane to $C_2$-hydrocarbons over the catalyst prepared in EXAMPLE-1 at different process conditions (Feed: a mixture of pure methane and $O_2$)

| Temperature (°C.) | Space Velocity ($cm^3 \cdot g^{-1} \cdot h^{-1}$) | $CH_4/O_2$ ratio | $CH_4$ conversion (%) | $C_2$-Selectivity (%) | $C_{2+}$ Selectivity (%) | $\frac{C_2H_4}{C_2H_6}$ ratio | $C_{2+}$ Productivity ($mmol \cdot g^{-1} \cdot h^{-1}$) | Concentration of $C_2H_4$ in (mol %) products (after removal of water) |
|---|---|---|---|---|---|---|---|---|
| 751 | 21,000 | 8.0 | 20.1 | 70.8 | 79.2 | 0.95 | 65.7 | 3.6 |
| 750 | 10,500 | 8.0 | 21.4 | 67.9 | 76.9 | 1.34 | 33.9 | 4.4 |
| 752 | 10,500 | 6.0 | 24.5 | 67.8 | 71.1 | 1.5 | 35.0 | 4.9 |
| 750 | 10,500 | 4.0 | 29.8 | 57.5 | 65.1 | 1.8 | 36.4 | 5.9 |
| 753 | 10,500 | 3.0 | 38.1 | 49.0 | 55.9 | 2.4 | 37.4 | 7.0 |
| 699 | 5,100 | 8.0 | 16.7 | 66.3 | 75.1 | 0.91 | 12.6 | 2.7 |
| 651 | 5,100 | 8.0 | 8.8 | 62.4 | 65.4 | 0.40 | 5.8 | 0.7 |

TABLE 2

Results on oxidative coupling of methane to $C_2$-hydrocarbons over the catalyst prepared in EXAMPLE-4 at different process conditions (Feed: a mixture of pure methane and $O_2$)

| Temperature (°C.) | Space Velocity ($cm^3 \cdot g^{-1} \cdot h^{-1}$) | $CH_4/O_2$ ratio | $CH_4$ Conversion (%) | $C_2$-Selectivity (%) | $C_{2+}$ Selectivity (%) | $\frac{C_2H_4}{C_2H_6}$ ratio | $C_{2+}$ Productivity ($mmol \cdot g^{-1} \cdot h^{-1}$) |
|---|---|---|---|---|---|---|---|
| 750 | 5,200 | 8.0 | 20.7 | 70.5 | 78.7 | 1.0 | 16.6 |
| 700 | 5,150 | 8.0 | 11.0 | 73.0 | 78.4 | 0.6 | 8.7 |
| 749 | 10,400 | 8.0 | 17.1 | 72.8 | 80.1 | 0.9 | 28.0 |
| 751 | 10,500 | 4.0 | 22.0 | 65.8 | 72.1 | 1.0 | 29.7 |
| 750 | 10,500 | 3.0 | 23.3 | 60.0 | 65.4 | 1.1 | 26.8 |

TABLE 3

Results on oxidation coupling of methane to $C_2$-hydrocarbons over the catalyst prepared in EXAMPLE-6 at different process conditions (Feed: a mixture of pure methane and $O_2$)

| Temperature (°C.) | Space Velocity ($cm^3 \cdot g^{-1} \cdot h^{-1}$) | $CH_4/O_2$ ratio | $CH_4$ Conversion (%) | $C_2$-Selectivity (%) | $C_{2+}$ Selectivity (%) | $\frac{C_2H_4}{C_2H_6}$ ratio | $C_{2+}$ Productivity ($mmol \cdot g^{-1} \cdot h^{-1}$) |
|---|---|---|---|---|---|---|---|
| 752 | 5,100 | 8.0 | 18.1 | 71.5 | 81.2 | 0.7 | 14.7 |
| 750 | 10,500 | 8.0 | 17.5 | 70.2 | 78.3 | 0.6 | 28.3 |
| 749 | 10,300 | 4.0 | 19.0 | 64.1 | 70.2 | 0.6 | 24.5 |
| 751 | 10,200 | 3.0 | 21.9 | 57.6 | 62.1 | 0.7 | 23.2 |

TABLE 4

Results on oxidation coupling of methane to $C_2$-hydrocarbons over the catalyst prepared in EXAMPLE-8 at different process conditions (Feed: a mixture of pure methane amd $O_2$)

| Temperature (°C.) | Space Velocity ($cm^3 \cdot g^{-1} \cdot h^{-1}$) | $CH_4/O_2$ ratio | $CH_4$ Conversion (%) | $C_2$-Selectivity (%) | $C_{2+}$ Selectivity (%) | $\frac{C_2H_4}{C_2H_6}$ ratio | $C_{2+}$ Productivity ($mmol \cdot g^{-1} \cdot h^{-1}$) |
|---|---|---|---|---|---|---|---|
| 750 | 5,100 | 8.0 | 17.7 | 66.2 | 74.5 | 0.8 | 13.2 |
| 751 | 10,300 | 8.0 | 20.3 | 63.1 | 71.2 | 0.7 | 29.2 |
| 753 | 20,500 | 8.0 | 17.8 | 67.2 | 75.2 | 0.6 | 53.9 |
| 755 | 10,300 | 4.0 | 30.4 | 53.8 | 60.8 | 1.0 | 34.0 |
| 752 | 10,300 | 3.0 | 37.3 | 47.1 | 53.2 | 1.2 | 34.2 |

TABLE 5

Results on oxidative coupling of methane to $C_2$-hydrocarbons over the catalyst prepared in EXAMPLE 10 at different process conditions (Feed: a mixture of pure methane and $O_2$)

| Temperature (°C.) | Space Velocity (cm$^3 \cdot$ g$^{-1} \cdot$ h$^{-1}$) | CH$_4$/O$_2$ ratio | CH$_4$ Conversion (%) | C$_2$-Selectivity (%) | C$_{2+}$ Selectivity (%) | $\frac{C_2H_4}{C_2H_6}$ ratio | C$_{2+}$ Productivity (mmol $\cdot$ g$^{-1} \cdot$ h$^{-1}$) |
|---|---|---|---|---|---|---|---|
| 747 | 5,100 | 8.0 | 18.1 | 49.3 | 71.1 | 1.3 | 12.9 |
| 700 | 5,100 | 8.0 | 11.1 | 43.4 | 48.9 | 0.6 | 5.4 |
| 750 | 10,300 | 8.0 | 16.9 | 51.2 | 62.3 | 1.0 | 21.3 |
| 753 | 10,300 | 8.0 | 40.1 | 36.2 | 53.1 | 2.1 | 36.7 |

The Main Advantages of the Invention are (i) The starting materials used for the preparation of Li-promoted MgO catalyst are magnesium acetate and lithium acetate as precursors for MgO and Li, respectively. Since, these catalyst precursors are high purity, crystalline and well defined chemicals, a highly reproducible Li-promoted MgO catalyst could be prepared by the present process.

(ii) Because of melting of both the catalyst precursors (i.e. magnesium acetate and lithium acetate) at and above 80° C., there is a thorough mixing of the two catalyst component elements forming a homogeneous mixture of the catalyst precursors, which on calcination at higher temperatures decomposes yielding Li-promoted MgO catalyst with uniform ditribution of the promoter (i.e. Li) throughout the MgO matrics.

(iii) The Li-promoted MgO catalyst prepared by the process of present invention shows no loss of its catalytic activity and selectivity in oxidative coupling of methane to ethane and ethylene for a long period (at least for 15 hours).

(iv) The Li-promoted MgO catalyst prepared by the process of present invention has high $CO_2$ content in the form of $CO_3=$ions distributed throughout the catalyst, which is responsible for the stability or long life of the catalyst. The $CO_3=$ions are formed during the calcination of catalyst precursors by decomposition of acetate ions.

(v) The Li-promoted MgO catalyst prepared by the process of present invention shows high methane conversion activity, very high selectivity for ethane and ethylene and also high productivity for ethane and ethylene in oxidative coupling of methane to ethane and ethylene.

We claim:

1. A process for preparation of an improved Li-promoted MgO catalyst useful for oxidative coupling of methane to ethane and ethylene, in presence of free oxygen, which comprises (i) mixing thoroughly powdered magnesium acetate and lithium acetate, which are catalyst precursors, with Li/Mg mole ratio of 0.01-1.0 with or without water, the $H_2O$/magnesium acetate weight ratio being in the range of 0-5.0, (ii) heating the mixture, while stirring, to dryness at a temperature of about 80°-300° C., (iii) powdering and calcining the dried mixture at a temperature of about 500°-1000° C. in presence of air, $O_2$, $CO_2$, inert gas or their mixture or under vacuum for about 1-100 h and (iv) making pellets, extrudates, or granules of the catalyst of required size.

2. A process as claimed in claim 1 wherein the Li/Mg mole ratio ranges from about 0.02 to 0.5.

3. A process as claimed in claim 1 wherein the $H_2O$/magnesium acetate weight ratio ranges from 0.0 to 1.0.

4. A process as claimed in claim 1 wherein the temperature of heating the mixture of catalyst precursors ranges from 100° to 150° C.

5. A process as claimed in claim 1 wherein the calcination temperature ranges from 700° to 800° C.

6. A process as claimed in claim 1 wherein the atmosphere for the calcination is static air or air containing about 2-20 mole % $CO_2$.

7. A process as claimed in claim 1 wherein the period of calcination of the dried mixture of the catalyst precursors ranges from 2 to 20 hours.

* * * * *